(12) United States Patent
Boling

(10) Patent No.: US 7,283,856 B2
(45) Date of Patent: Oct. 16, 2007

(54) IMPLANTABLE LEAD SYSTEM WITH SEED ELECTRODES

(75) Inventor: C. Lance Boling, San Jose, CA (US)

(73) Assignee: Neuro Pace, Inc., Mountain View, CA (US)

( * ) Notice: Subject to any disclaimer, the term of this patent is extended or adjusted under 35 U.S.C. 154(b) by 276 days.

(21) Appl. No.: 10/821,789

(22) Filed: Apr. 9, 2004

(65) Prior Publication Data

US 2005/0228249 A1 Oct. 13, 2005

(51) Int. Cl.
*A61B 5/04* (2006.01)
*A61N 1/05* (2006.01)

(52) U.S. Cl. ...................... 600/378; 607/116
(58) Field of Classification Search ................ 600/378; 607/116
See application file for complete search history.

(56) References Cited

U.S. PATENT DOCUMENTS

| | | | | |
|---|---|---|---|---|
| 3,722,005 A | * | 3/1973 | Cowland | 623/25 |
| 3,964,470 A | * | 6/1976 | Trombley | 600/377 |
| 6,006,124 A | * | 12/1999 | Fischell et al. | 600/378 |
| 6,016,449 A | | 1/2000 | Fischell et al. | |
| 6,529,774 B1 | * | 3/2003 | Greene | 600/545 |
| 6,662,035 B2 | * | 12/2003 | Sochor | 600/378 |
| 2002/0116042 A1 | * | 8/2002 | Boling | 607/122 |
| 2005/0137647 A1 | * | 6/2005 | Wallace et al. | 607/45 |

OTHER PUBLICATIONS

Ajmone-Marsan, C., Electrocorticography: Historical Comments on its Development and the Evolution of its Practical Applications, Electroencephalogr. Clin. Neurophysiol. Suppl 1998, 48: 10-16.
Black, P.M. & Ronner, S.F.,Cortical Mapping for Defining the Limits of Tumor Resection, Neurosurgery 1987, 20 : 914-919.
Cooper, I.S. & Upton, A.R.M., Effects of Cerebellar Stimulation on Epilepsy, the EEG and Cerebral Palsy in Man, Electroencephalogr. Clin. Neurophysiol. Suppl. 1978, 34: 349-354.

* cited by examiner

*Primary Examiner*—Lee S. Cohen

(57) ABSTRACT

A medical electrical lead system for neurological applications has a distal portion having a plurality of independently positionable seed electrodes, each of which may be connected via an interface to an implantable medical device. The interface allows the seed electrodes to be positioned, then excess wire trimmed, facilitating simplified connection of multiple independent electrodes to a single device. Seed electrodes according to the invention are small, have relatively low mass, and are minimally destructive of surrounding tissue.

7 Claims, 7 Drawing Sheets

IMPLANTABLE LEAD SYSTEM WITH SEED ELECTRODES

FIELD OF THE INVENTION

The invention is related to implantable medical leads, and more particularly to implantable electrical leads used to sense electrographic signals from a patient's brain or to apply electrical stimulation to the brain.

BACKGROUND OF THE INVENTION

In the medical diagnosis and treatment of various brain disorders, including epilepsy, Parkinson's disease, sleep disorders, and psychiatric ailments, it is customary and frequently useful to analyze electrical signals originating in the brain. For a review of this technology, see Ajmone-Marsan, C., Electrocorticography: Historical Comments on its Development and the Evolution of its Practical Applications, Electroencephalogr. Clin. Neurophysiol. Suppl. 1998, 48:10-16; there are numerous other applications. These electrographic signals are commonly known as electroencephalogram (EEG) signals when originating or received at the surface of the brain, such as from scalp electrodes, or electrocorticogram (ECoG) signals when originating or received below the surface of the brain, such as from intracranial electrodes. The term "EEG" will be used generically herein to refer to both types of signals.

It is also becoming accepted to apply electrical stimulation to various structures of the brain for both diagnostic and therapeutic purposes. For an exemplary diagnostic application, see Black, P. M. & Ronner S. F., Cortical Mapping for Defining the Limits of Tumor Resection, Neurosurgery 1987, 20:914-919, which addresses the use of electrical stimulation via deep brain electrodes to identify functional portions of the brain prior to and as a planning stage in surgical resection. For an example of a therapeutic application, see Cooper, I. S. & Upton, A. R. M., Effects of Cerebellar Stimulation on Epilepsy, the EEG and Cerebral Palsy in Man, Electroencephalogr. Clin. Neurophysiol. Suppl. 1978, 34: 349-354. In both of these examples, acutely implanted brain electrodes are connected to external equipment.

It is also contemplated that chronic electrical stimulation can be used as a direct treatment for disorders such as epilepsy. See, e.g., U.S. Pat. No. 6,016,449 to Fischell, et al., which describes an implantable neurostimulator that is coupled to relatively permanent deep brain electrodes.

Although it is frequently possible to employ scalp electrodes for certain types of EEG monitoring and analysis, it has been found that ambient electrical noise (such as from the 50/60 Hz power system) can adversely impact signal-to-noise ratio, and certain signal components of interest may be filtered out by the patient's intervening cranium and scalp tissue. Moreover, precise localization is less feasible with scalp electrodes.

Accordingly, intracranial signal analysis, that is, the consideration of signals that originate from within a patient's cranium, whether by internal or external apparatus, is best accomplished with brain surface electrodes, such as strip and grid electrodes, cortical depth leads, or some combination of surface electrodes and depth leads.

Typical brain surface strip and grid electrode arrays consist of flat, disk-shaped electrodes that are placed on the surface of the patient's brain. In a typical strip or grid electrode array, each electrode has an exposed diameter of approximately 3 mm (or ⅛ inch), and the electrodes are distributed along a line (for a strip electrode array) or in a rectangular grid (for a grid electrode array) at a pitch of approximately 10 mm.

Unfortunately, brain surface strip and grid electrode arrays have a tendency, particularly with long-term chronic use, to move away from the surface of the brain. This can be caused by atrophy or other mechanisms associated with cerebrospinal fluid (CSF) dynamics. The result is frequently unsatisfactory or intermittent electrical contact between the electrodes and the desired brain tissue. It frequently requires further surgery (with the associated risks for the patient) or electronic compensation for the change in characteristics (with a potentially harmful increase in stimulation current being delivered to the brain, or at minimum, decreased signal-to-noise ratio), and may result in long-term performance deterioration. There is no known acceptable way to anchor a traditional strip or grid electrode array to the surface of the brain. While the electrode may be anchored to the patient's cranium or dura mater, the brain tends to recede from these structures in certain cases. Moreover, the electrodes are spaced evenly along a line or grid, and while it is possible to orient a strip or grid electrode array in a desired manner, it is generally not possible to position the individual electrodes independently.

Typical brain depth leads are flexible small-diameter (usually 1-1.5 mm) round leads having distal electrodes. It is known for depth leads to have multiple independent distal electrodes on the same lead shaft, but such electrodes are generally located coaxially along a distal portion of the shaft. It is difficult, and usually impractical, to attempt to position the individual electrodes independently.

Accordingly, it would be desirable to have an implantable medical electrical lead that provides the advantages of both surface electrodes and depth leads, along with other advantages. Such an electrical lead would have multiple distal electrodes that are independently positionable near the surface of the brain or in deep brain structures, and would remain in contact with the desired neural tissue regardless of atrophy or other adverse conditions.

SUMMARY OF THE INVENTION

A medical electrical lead system in accordance with the present invention addresses the shortcomings of existing implantable lead systems by providing multiple independently positionable "seed electrodes". A seed electrode system according to the invention has independent leads that have minimal excess slack, and thus are resistant to breakage and erosion, and take up little space. The seed electrodes are small and have minimal mass, thereby avoiding inertial movement, and resisting changes due to brain atrophy. Seed electrodes according to the invention are relatively easy to implant, stay in place, and are believed to be less traumatic than traditional depth leads (thereby enabling new surgical strategies, including implanting many seed electrodes and interfacing relatively few of them to a device).

The inventive medical electrical lead system has a multi-conductor proximal segment configured to connect to an implantable medical device or external equipment. At its distal end, the proximal segment connects to an interface module, which in one embodiment of the invention also serves as a burr hole cover. The interface module connects and maps one or more of the conductors in the proximal segment to one or more individually positionable insulated conductor filaments, each of which has a distal "seed electrode" adapted for implantation according to the invention. In one embodiment of the invention, the interface module includes an active multiplexer circuit, enabling more seed electrodes to be coupled to a medical device than the device would otherwise support.

An introducer apparatus is specially configured to implant the seed electrodes of the present invention. The introducer apparatus is adapted to interface with one or more commonly used Stereotactic head frame assemblies and to accurately position the seed electrodes of the invention within the patient's brain. In an embodiment of the invention, the introducer apparatus includes a relatively rigid insertion cannula, a push tube, and a depth calibrating spacer. The seed electrode is releasably attached to the insertion cannula such that the push tube can be manipulated to break the attachment and leave the seed electrode in place while the cannula is retracted.

With a lead system in accordance with the present invention, it is possible to realize several additional advantages. With plural individually positionable distal electrodes, it is possible to reach a larger number of separate brain sites while limiting the number of leads necessary to do so. The number of leads connected to an external apparatus or implanted neurostimulator (or other device) is minimized, thereby improving the ease of treating the patient, improving ease of lead management, reducing the possibility of lead breakage, and reducing the possibility of discomfort or erosion under the patient's scalp.

A seed electrode system according to the invention can be used for sensing applications, stimulation applications, or dual-purpose applications.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
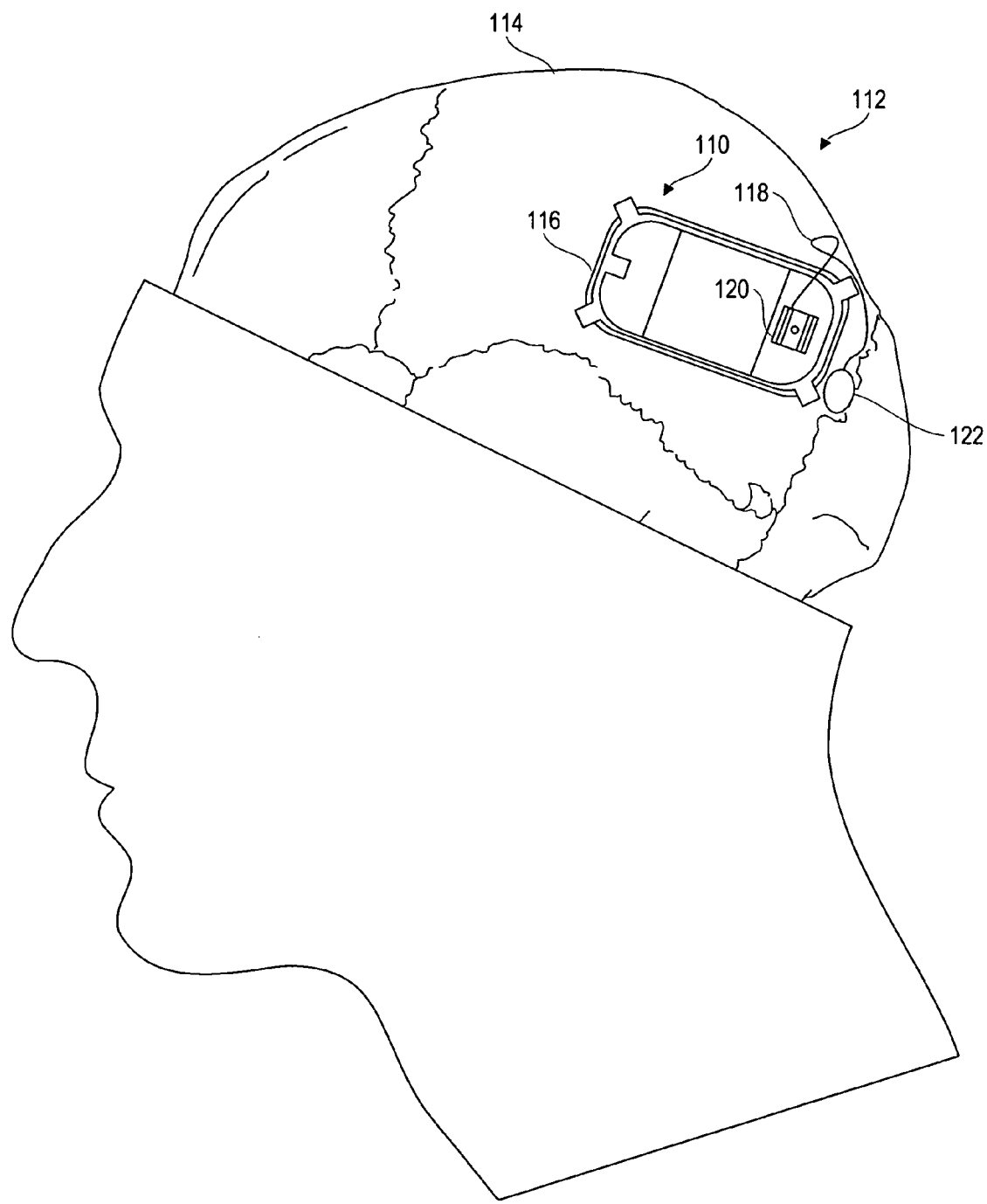
FIG. 1 is an illustration showing the use of a neurostimulator, lead, and interface according to the invention in an exemplary patient cranium.

An implantable neurostimulator device 110 according to the invention, as implanted intracranially in a patient 112, is illustrated in FIG. 1. The device 110 is affixed in the patient's cranium 114 by way of a ferrule 116. The ferrule 116 is a structural member adapted to fit into a cranial opening, attach to the cranium 114, and retain the device 110.

To implant the device 110, a craniotomy is performed in the parietal bone anterior to the lambdoidal suture to define an opening slightly larger than the device 110. The ferrule 116 is inserted into the opening and affixed to the cranium 114, ensuring a tight and secure fit. The device 110 is then inserted into and affixed to the ferrule 116.

As shown in FIG. 1, the device 110 is attached to a lead 118 by way of a lead connector 120 adapted to receive one or more electrical leads, such as the illustrated lead 118. The lead connector 120 acts to physically secure the lead 118 to the device 110, and facilitates electrical connection between a conductor in the lead 118 coupling a seed electrode according to the invention to circuitry within the device 110. The lead connector 120 accomplishes this in a substantially fluid-tight environment with biocompatible materials.

A proximal portion of the lead 118, as illustrated, and other leads for use in a system or method according to the invention, is a flexible elongated member having one or more conductors. As shown, the lead 118 is coupled to the device 110 via the lead connector 120, and is generally situated on the outer surface of the cranium 114 (and under the patient's scalp), extending between the device 110 and a seed electrode interface 122 taking the form of a burr hole cover, where the lead 118 enters the cranium 114 and is coupled to one or more seed electrodes implanted in desired locations in the patient's brain (such as the GPi, the thalamus, or the subthalamic nucleus). If the length of the lead 118 is substantially greater than the distance between the device 110 and the interface 122, any excess may be urged into a coil configuration under the scalp.

The device 110 includes a durable outer housing fabricated from a biocompatible material. Titanium, which is light, extremely strong, and biocompatible, is used in analogous devices, such as cardiac pacemakers, and would serve advantageously in this context. As the device 110 is self-contained, the housing encloses a battery and any electronic circuitry necessary or desirable to provide the functionality described herein, as well as any other features. As will be described in further detail below, a telemetry coil may be provided outside of the housing (and potentially integrated with the lead connector 120) to facilitate communication between the device 110 and external devices.

The neurostimulator configuration described herein and illustrated in FIG. 1 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 116 used for implantation allows the craniotomy to be performed and fit verified without the possibility of breaking the device 110, and also provides protection against the device 110 being pushed into the brain under external pressure or impact. A further advantage is that the ferrule 116 receives any cranial bone growth, so at explant, the device 110 can be replaced without removing any bone screws—only the fasteners retaining the device 110 in the ferrule 116 need be manipulated.

Figure 2:
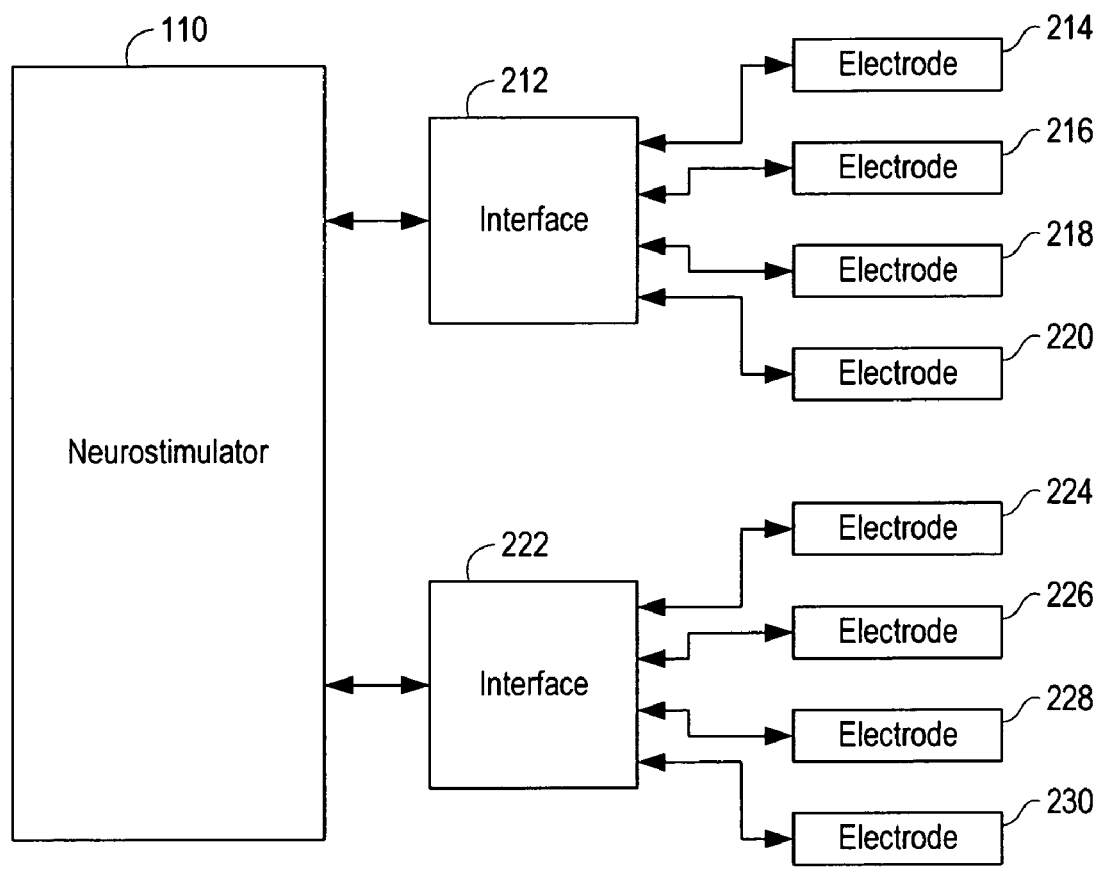
FIG. 2 is a block diagram illustrating the use of two seed electrode interfaces and eight seed electrodes in a system according to the invention.
Figure 3:
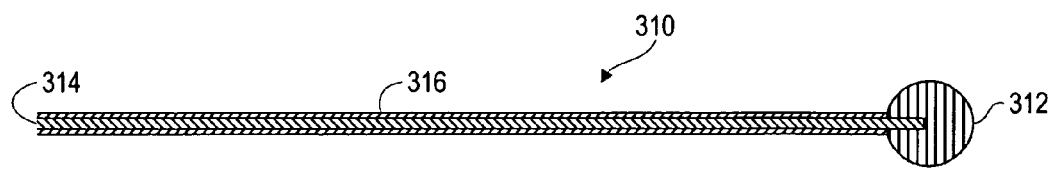
FIG. 3 is a cross-sectional illustration showing an exemplary seed electrode and lead assembly according to the invention.

FIG. 2 is a block diagram illustrating how the implantable neurostimulator device 110 (FIG. 1) is coupled to two interface modules in the disclosed embodiment of the invention. As illustrated in FIG. 1, the device 110 includes a lead connector 120 adapted to receive two multi-conductor leads, although only one lead 118 is illustrated in FIG. 1. Accordingly, one lead is used to couple a first seed electrode interface 212 to device 110. In turn, the first seed electrode interface 212 is coupled to four seed electrode assemblies, 214, 216, 218, and 220. Each of the seed electrode assemblies 214-220 is electrically coupled to the device 110 through the first interface 212 as illustrated. Similarly, a second seed electrode interface 222 electrically couples four seed electrode assemblies 224, 226, 228, and 230 to the device 110. It should be observed that other configurations of the device 110 and one or more interfaces and seed electrode assemblies are possible. In one embodiment of the invention, seed electrode assemblies can be connected directly to the device 110. However, and interface (such as the two interfaces 212 and 222) interposed between the device 110 and any seed electrodes will allow the device 110 to be explanted and replaced, or additional seed electrodes added, without the need to disturb existing seed electrode assemblies FIG. 3 depicts an exemplary seed electrode assembly 310 of the type illustrated in block form in FIG. 2. The illustrated seed electrode assembly 310 includes a metallic seed electrode 312 at its distal end. In the disclosed embodiment, the seed electrode 312 is about 1 mm in diameter and is fabricated from a biocompatible conductive material such as platinum or a platinum-iridium alloy. The seed electrode 312 is coupled to a length of wire 314, typically also a biocompatible material such as Pt or Pt—Ir. The wire 314 is significantly thinner than the diameter of the seed electrode 312 (and in the disclosed embodiment has a diameter of approximately 0.1 mm) and is covered with an insulating coating 316. The disclosed wire 314 has a length of at least 30 cm, and may be cut to a desired shorter length upon use. It is possible to use shorter or longer lengths without departing from the scope of the invention.

The seed electrode 312 and the wire 314 are electrically coupled to each other; typically the two pieces may be welded or crimped together. The wire 314 may be a single strand of conductive material, or if some compliance is desired, may comprise plural strands of thinner material wound together. The seed electrode assembly 310 should be strong enough to resist fracture and failure during the implant process and chronic use by the patient thereafter; this principle would guide selection of materials, dimensions, and tolerances by a practitioner of ordinary skill.

Figure 4:
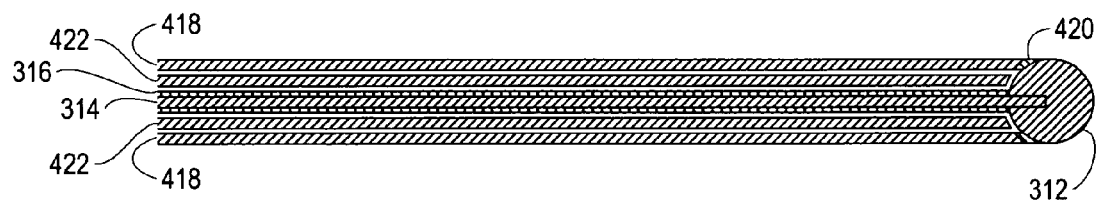
FIG. 4 is a cross-sectional illustration showing the seed electrode and lead assembly of FIG. 3 in conjunction with an insertion cannula and push tube according to the invention.

In FIG. 4, the seed electrode assembly 310 (FIG. 3) is shown in relation to other parts of a system according to the invention; these parts are used to implant the seed electrode assembly 310. Specifically, the seed electrode 312 is disposed at a distal end of a tube-shaped insertion cannula 418 of substantially the same outer diameter as the seed electrode 312. The seed electrode 312 is mechanically coupled to the distal end of the insertion cannula 418 via a quantity of releasable biocompatible adhesive 420. The wire 314 (with its insulating coating 316) is threaded longitudinally through a bore of the insertion cannula 418. The insertion cannula is fabricated from a relatively rigid biocompatible material that is capable of tunneling through the patient's brain.

A relatively rigid push tube 422 is positioned between (and coaxial with) the wire 314 and the insertion cannula 418. The push tube does not appreciably adhere to the seed electrode 312 or the cannula 418; rather, it is preferably free to move longitudinally when manipulated by a clinician. As will be discussed in further detail below (in connection with FIG. 8), the push tube 422 is used to disengage the seed electrode 312 from the cannula 418 when a desired position within the patient's brain is reached.

The cannula 418 and push tube 422 are fabricated from a material suitable for use in acute surgical settings, such as stainless steel. As described above, the outer diameter of the insertion cannula 418 is generally defined by the diameter of the seed electrode 312; other inner and outer diameters (for the cannula 418 and push tube, for example) may be determined on a relative basis by considering the desired mechanical characteristics of a system according to the invention as would be understood by a practitioner of ordinary skill in the art.

Figure 5:
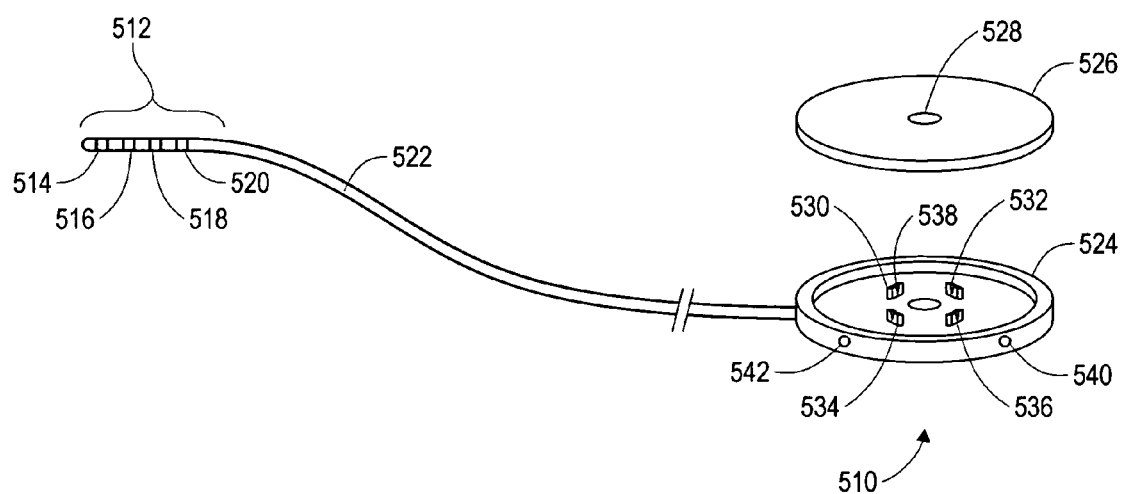
FIG. 5 is an illustration of an exemplary proximal lead end and seed electrode interface according to the invention.

An embodiment of a seed electrode interface 510 is illustrated in FIG. 5. In the disclosed embodiment, the interface 510 is a relatively thin disc-shaped unit coupled to a proximal terminal end 512 adapted to be coupled to a neurostimulator (such as the device 110 of FIG. 1). The proximal terminal end 512 includes four ring terminals 514, 516, 518, and 520, each of which is electrically coupled to a conductor embedded within a substantially cylindrical lead body 522. The lead body 522 connects each of the ring terminals 514-520 to a housing 524 of the interface 510. In the disclosed embodiment of the invention, the lead body 522 is fabricated from biocompatible silicone, and the ring terminals 514-520 are Pt—Ir alloy. The lead body 522 has a diameter between 1.0 and 1.5 mm and a length between 5 and 20 cm, although other dimensions are possible.

The interface 510 further includes a cover 526 adapted to fit the housing 524. In the disclosed embodiment, the cover defines an aperture 528 configured to receive a fastener to attach the cover 526 to the housing 524, such as a captive screw (not shown). The cover 526 is intended to substantially exclude body fluids and growth from entering an interior portion of the housing, although it is to be expected that some leakage is probable.

The interface 510, within the housing 524, includes four punchdown terminals 530, 532, 534, and 536. Each of the punchdown terminals 530-536 includes a conductive blade electrically coupled to a corresponding ring terminal 514-520 at the proximal terminal end 512 of the interface 510.

Accordingly, then, one or more seed electrode assemblies (as in the seed electrode assembly 310 of FIG. 3) may be coupled to the interface 510; the disclosed embodiment of the interface 510 receives up to four seed electrode assemblies. A single seed electrode assembly 310 (FIG. 3) is connected to the interface 510 by routing its wire 314 through a hole (such as one of the two visible holes 540 and 542) in the housing, positioning the wire 314 over a desired and selected punchdown terminal one of the punchdown terminals 530-536), and pressing the wire 314 down into the selected punchdown terminal at substantially any location along the length of the wire 314. A tool may be provided for the purpose; punchdown terminals and tools are generally understood by practitioners of ordinary skill in the art to which this invention pertains.

As is well known, the act of pushing the wire 314 down into a punchdown terminal will cause the insulating cover 316 over the wire 314 to be penetrated by the blade of the punchdown terminal, enabling electrical conduction between the blade and the wire 314, and hence a closed electrical circuit between one of the ring terminals 514-520 and the seed electrode 312. If there is any unused length of wire 314 after it is connected to the interface 510, it may be trimmed. It should be apparent that after trimming, different custom lengths of wire 314 may be present, thereby reducing any undesired slack in wires leading up to the seed electrode 312.

The process set forth above is repeated for up to four seed electrode assemblies in a single interface, or eight seed electrode assemblies with two interfaces (provided the disclosed embodiment of the device 110 is used; as stated above, other configurations are possible). It will be recognized that if two interfaces are used, they may be positioned in different locations. In an embodiment of the invention, the interface 510 includes active multiplexing circuitry to allow a relatively large number of seed electrode assemblies to be driven by or responsive to a relatively small number of input/output channels on the device.

In an embodiment of the invention, the cover 526 defines a lower surface adapted to mechanically clamp a short portion of seed electrode assemblies within the housing 524 when the cover 526 is engaged with the housing 524; this provides additional strain relief on the seed electrode assemblies and serves to exclude fluids and tissue growth to some extent.

The interface 510 illustrated in FIG. 5 is adapted to be positioned between the patient's scalp and cranium; suture holes or other fastening means may be provided as desired to anchor the interface 510 in a preferred position.

Figure 6:
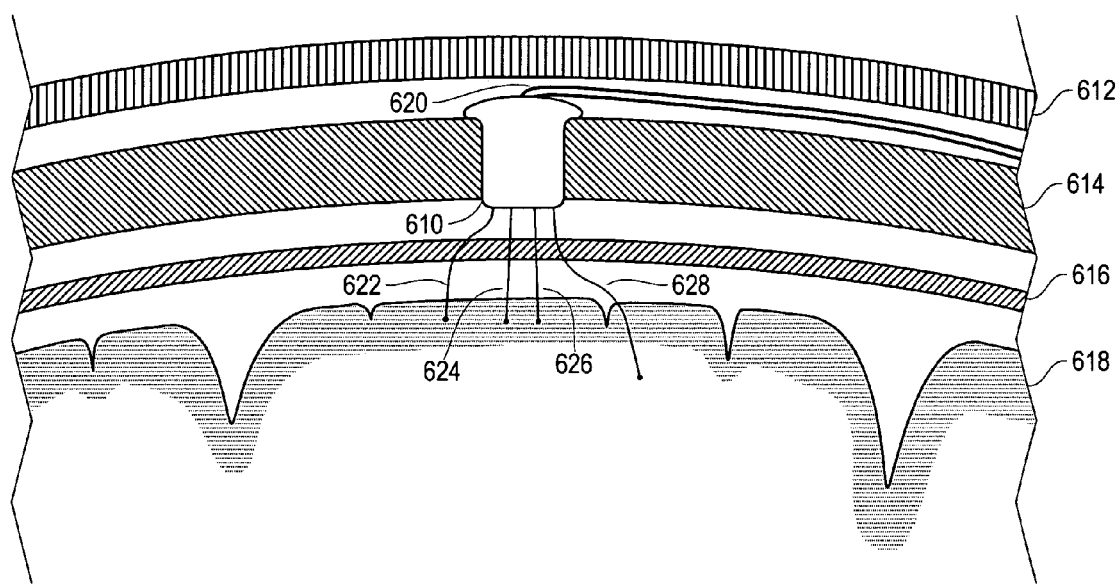
FIG. 6 depicts the use of a set of four seed electrodes according to the invention in an exemplary section of a patient's head, including the patient's brain, dura mater, and cranium, where the seed electrode interface constitutes at least a part of a burr hole cover.

FIG. 6 illustrates an embodiment of the interface 510 incorporated into a burr hole cover assembly 610. As illustrated, In general, an interface 510 according to the invention is advantageously situated below a patient's scalp 612, and in the illustrated embodiment the burr hole cover 610 (incorporating the functions of the interface 510) extends through the patient's cranium 614, and seed electrode assemblies penetrate the dura mater 616 to access the patient's cortex 618.

As illustrated, and consistent with the illustration of FIG. 6, the disclosed burr hole cover 610 has a lead body 620 connected to a neurostimulator (such as the device 110, not shown) and accommodates four seed electrode assemblies 622, 624, 626, and 628, which are shown inserted into desired electrode sites. Contrary to the illustration of FIG. 5, this embodiment receives the lead body 620 at a top location and the seed electrode assemblies 622-628 at a bottom location. Choosing desired electrode sites may be performed at any appropriate stage of the surgical procedure, including presurgically in an operative planning stage; intraoperatively after a craniotomy have been performed or a burr hole has been made; or intraoperatively after one or more other procedures, such as functional mapping, have been performed.

Each of the seed electrode assemblies 622-628 is inserted a short distance into the cortex 618, enough to ensure their distal electrodes are fully embedded in neural tissue. This configuration can be adapted to serve as a replacement for a strip electrode, with four electrodes inserted shallowly in the cortex in an essentially collinear configuration. Other configurations (including different implantation depths and non collinear configurations) are, of course, possible, and are described elsewhere herein.

The seed electrode assemblies 622-628 are preferably inserted into the cortex relatively perpendicular to the surface of the brain (although different trajectories are possible and at times clinically desirable, as determined in surgical planning); this arrangement minimizes tissue damage and orients the electrodes consistently with respect to each other. In the absence of external forces, the distal end segments will ordinarily remain implanted in the desired electrode sites without any affixation means.

By way of explanation, it is anticipated that implantation of the seed electrode assemblies 622-628 will be performed before the burr hole cover 610 is in place. After the seed electrode assemblies 622-628 are positioned, their corresponding wires are routed into the burr hole cover 610, the burr hole cover 610 is placed and affixed, and the wires for the seed electrode assemblies 622-628 are connected to punchdown terminals within the burr hole cover 610 and trimmed as desired. The cover 526 and housing 524 are then attached to each other, and the lead body 620 is then routed to the device 610, over the cranium 614, as desired.

Figure 7:
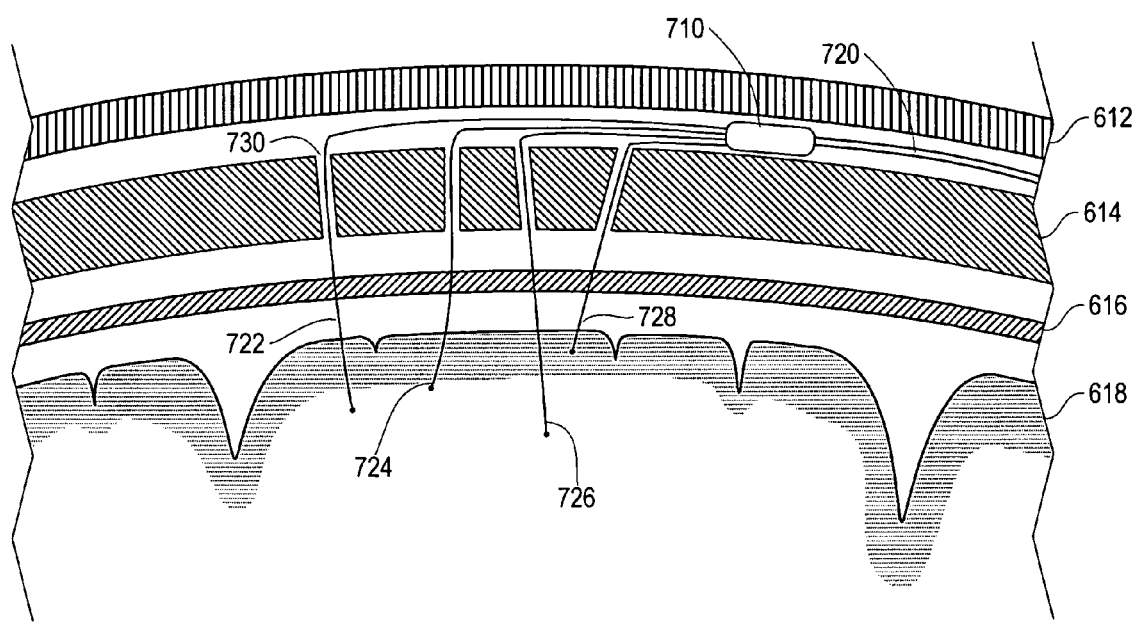
FIG. 7 depicts the use of a set of four seed electrodes according to the invention in an exemplary section of a patient's head, including the patient's brain, dura mater, and cranium, where the seed electrode interface constitutes a subcutaneous interface positioned between the patient's scalp and cranium.

FIG. 7 illustrates a subcutaneous module 710 form of the interface 510. It does not function as a burr hole cover, but otherwise functions similarly to the embodiment of FIG. 6. The subcutaneous module 710 is positioned between the patient's scalp 612 and cranium 614, and if desired, is affixed in position or embedded into a space defined by the cranium 614. A lead body 720 connects the subcutaneous module 710 to a neurostimulator (as in the device 110, not shown). The subcutaneous module 710 receives four seed electrode assemblies 722, 724, 726, and 728. Because the subcutaneous module 710 does not function as a burr hole cover, the seed electrode assemblies 722-728 are connected to the module 710 above the cranium 614. Accordingly, each of the seed electrode assemblies 722-728 (such as a first seed electrode assembly 722) will penetrate the cranium 614 through a relatively small opening (such as a first opening 730) defined in the cranium and formed via twist drill, for example. Each relatively small opening may be sealed with a small quantity of biocompatible adhesive, such as certain cyanoacrylate and epoxy materials.

In the disclosed embodiment, the seed electrode assemblies 722-728 are inserted at different locations, with different trajectories and different depths. Each of the seed electrode assemblies 722-728 is independently positionable.

Figure 8:
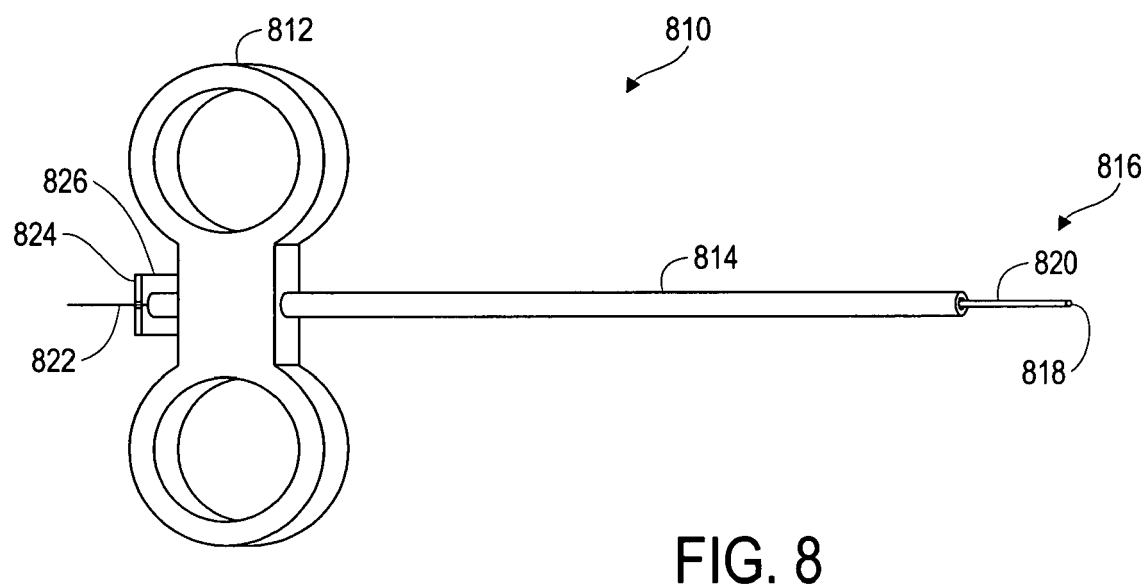
FIG. 8 shows an exemplary introducer apparatus according to the invention, used for positioning the seed electrode and lead assembly of FIG. 3 in a patient's brain.

FIG. 8 illustrates an introducer apparatus 810 according to the invention, used to position seed electrodes in a patient's brain (or other) tissue. The introducer apparatus 810 includes a handle 812 and a spacer 814, and in an embodiment of the invention the spacer 814 is removable and replaceable with spacers of different lengths, and also can be coupled to a Stereotactic head frame or other equipment adapted to position the introducer apparatus 810 accurately and precisely. The spacer may be made of any relatively rigid material suitable for acute surgical use, such as stainless steel or any of various polymers.

A portion of a seed electrode assembly 816 protrudes from the spacer 814 at a proximal end of the introducer apparatus 810, to a length defined by the length of the spacer 814. A seed electrode 818 and a portion of an insertion cannula 820 are visible; the insertion cannula 820 fits snugly (but slidably) within the spacer 814 and is coupled to the handle 812. At a distal end of the apparatus 810, another portion of a seed electrode assembly 816 protrudes; a distal portion of a push tube 822 is visible. The push tube 822 is preferably held in place and prevented from unintended longitudinal motion by a clip 824, held in place by a flexible (and moveable) stanchion 826. When longitudinal motion of the push tube 822 (and hence the seed electrode 818) is desired, the stanchion 826 may be deflected and the clip 824 disengaged from the push tube 822.

In operation, a desired target site is identified either in surgical planning or intraoperatively. A Stereotactic head frame or other apparatus is fixed to the patient and adjusted to place the spacer 814 in line with a desired trajectory to the target site, such that the introducer apparatus 810, when the cannula 820 is inserted into the spacer 814, causes the seed electrode 818 to penetrate the tissue to a specified depth which may be slightly short of the target site.

When the target site is nearly reached, the push tube 822 and introducer apparatus 810 are manipulated (i.e., moved longitudinally with respect to one another) to apply force to the seed electrode 818 and separate it from the adhesive 420 (FIG. 4) coupling it to the cannula 820. The adhesive 420 effectively prevents the seed electrode 818 from inadvertent motion with respect to the cannula 820, but when the seed electrode 818 is appropriately placed, the push tube 822 enables the cannula 820 to be removed while the seed electrode 818 remains in place.

The foregoing surgical approach is deemed representative only; other methods of implanting a seed electrode system according to the invention, either with or without an introducer apparatus 810, are possible.

It should be observed that while the foregoing detailed description of various embodiments of the present invention is set forth in some detail, the invention is not limited to those details and an implantable medical electrical lead system made or used according to the invention can differ from the disclosed embodiments in numerous ways. In particular, it will be appreciated that embodiments of the present invention may be employed in many different applications for sensing or stimulation, not just in the brain. Leads according to the invention may have utility in connection with peripheral nerves, muscles, other portions of the body, and other applications. Hence, the appropriate scope hereof is deemed to be in accordance with the claims as set forth below.

What is claimed is:

1. A medical electrical lead system adapted to be at least partially implanted in a human patient, the lead system comprising:
 a plurality of seed electrodes, each of which seed electrodes is affixed to a conducting wire; and
 an implantable interface to electrically connect to each conducting wire at substantially any desired location along the length of the conducting wire;
 wherein the interface is adapted to provide a closed electrical circuit between each seed electrode and a medical device.

2. The medical electrical lead system of claim 1, wherein the implantable interface is configured as a burr hole cover.

3. The medical electrical lead system of claim 1, wherein the implantable interface is adapted to be positioned in a subcutaneous location.

4. The medical electrical lead system of claim 1, wherein the implantable interface is adapted to be positioned within brain tissue of the patient.

5. The medical electrical lead system of claim 1, wherein at least one of the seed electrodes has a substantially greater diameter than the conducting wire with which the at least one seed electrode is associated.

6. The medical electrical lead system of claim 1, wherein the interface comprises a plurality of punchdown terminals, each punchdown terminal adapted to make an electrical connection between a conducting wire and a seed electrode at substantially any location along the length of the conducting wire.

7. The medical lead system of claim 6, wherein each punchdown terminal comprises at least one blade.

* * * * *